US005744597A

United States Patent [19]

Chou et al.

[11] Patent Number: 5,744,597
[45] Date of Patent: Apr. 28, 1998

[54] STEREOSELECTIVE ANION GLYCOSYLATION PROCESS FOR PREPARING 2'-DEOXY-2',2'-DIFLUORONUCLEOSIDES AND 2'-DEOXY-2'-FLUORONUCLEOSIDES

[75] Inventors: Ta-Sen Chou; Cora S. Grossman; Larry Wayne Hertel; Richard E. Holmes; Charles D. Jones; Thomas E. Mabry, all of Indianapolis, Ind.

[73] Assignee: Eli Lilly and Company, Indianapolis, Ind.

[21] Appl. No.: 459,573

[22] Filed: Jun. 2, 1995

Related U.S. Application Data

[60] Division of Ser. No. 44,315, Apr. 7, 1993, abandoned, which is a continuation-in-part of Ser. No. 902,135, Jun. 22, 1992, abandoned.

[51] Int. Cl.$^6$ .......................... C07H 1/00; C07H 19/073; C07H 19/173
[52] U.S. Cl. ...................... 536/55.3; 536/27.1; 536/28.1
[58] Field of Search .................... 536/55.3, 27.1, 536/28.1

[56] References Cited

U.S. PATENT DOCUMENTS

| | | |
|---|---|---|
| 3,282,921 | 11/1966 | Verheyden et al. ............. 260/211 |
| 4,145,414 | 3/1979 | Kelly et al. .................. 424/180 |
| 4,145,531 | 3/1979 | Eckstein et al. .............. 536/26 |
| 4,211,773 | 7/1980 | Lopez et al. ................. 424/180 |
| 4,526,988 | 7/1985 | Hertel ........................ 549/313 |
| 4,625,020 | 11/1986 | Brundidge et al. ............ 536/18.2 |
| 4,751,221 | 6/1988 | Watanabe et al. ............. 514/46 |
| 4,808,614 | 2/1989 | Hertel ........................ 514/45 |
| 4,965,374 | 10/1990 | Chou et al. .................. 549/313 |
| 5,371,210 | 12/1994 | Chou ......................... 536/27.11 |

FOREIGN PATENT DOCUMENTS

| | | |
|---|---|---|
| 145978 | 6/1985 | European Pat. Off. . |
| 211354 | 2/1987 | European Pat. Off. . |
| 219829 | 4/1987 | European Pat. Off. . |
| 339161 | 11/1989 | European Pat. Off. . |
| 345751 | 12/1989 | European Pat. Off. . |
| 428109 | 5/1991 | European Pat. Off. . |
| 2125401 | 3/1984 | United Kingdom . |

OTHER PUBLICATIONS

Chem. Pharm. Bull., 11, 1470–72 (1963).
Chem. Pharm. Bull., 12, 1471–78 (1964).
Vorbruggen, et al., J. Org. Chem., 41(12), 2084–86 (1976).
Kazimierczuk, et al., J. Am. Chem. Soc., 106, 6379–82 (1984).
Seela, et al., Liebigs Ann. Chem., 895–901 (1989).
Reichman, et al., Carbohydr. Res., 42, 233–40 (1975).
Howell, et al., J. Org. Chem., 53, 85–88 (1988).
Comprehensive Organic Chemistry, Barton and Ollis Ed., 5, 60–67 (1979).
Davoll, et al., J. Am. Chem. Soc., 73, 1650–55 (1951).
Hilbert, et al., J. Am. Chem. Soc., 52, 2001–07 (1930).
Z. Chem., 4, 303–04 (1964).
Sanghvi, et al., Nucleosides & Nucleotides, 6(4), 761–74 (1987).
Koenigs, et al., Berichete Dent. Chem. Gesellschaft, 34, 957–981 (1901).
Prystas, et al., Coll. Czech. Chem. Comm., 31, 3990–4001 (1966).
Hoffer, et al., Chem. Ber., 93, 2777–81 (1960).
Wittenburg, et al., Chem. Ber., 101, 1095–1114 (1968).
Howard, et al., J. Am. Chem. Soc., 1052–54 (1947).
Hertel, et al., Nucleosides & Nucleotides, 8(5&6), 951–55 (1989).

Primary Examiner—Gary L. Kunz
Attorney, Agent, or Firm—Brian P. Barrett; David E. Boone

[57] ABSTRACT

A stereoselective anion glycosylation process for preparing beta- and alpha-anomer enriched 2', 2'-difluoro-2'-deoxynucleosides and 2'-deoxy-2'-fluoronucleosides by reacting an alpha- or beta-anomer enriched 2-deoxy-2-fluorocarbohydrate or 2-deoxy-2,2-difluorocarbohydrate with at least a molar equivalent of a salt of a nucleobase derivative in an inert solvent.

14 Claims, No Drawings

STEREOSELECTIVE ANION GLYCOSYLATION PROCESS FOR PREPARING 2'-DEOXY-2',2'-DIFLUORONUCLEOSIDES AND 2'-DEOXY-2'-FLUORONUCLEOSIDES

CROSS REFERENCE TO RELATED APPLICATION

This application is a division of application Ser. No. 08/044,315, filed Apr. 7, 1993, now abandoned, which is a continuation-in-part of application Ser. No. 07/902,135 filed Jun. 22, 1992, now abandoned.

BACKGROUND OF THE INVENTION

1. Field of the Invention

The invention pertains to the field of pharmaceutical chemistry and provides a stereoselective anion glycosylation process for preparing 2'-deoxy-2',2'-difluoronucleosides and 2'-deoxy-2'-fluoronucleosides.

2. State of the Art

Several synthetic nucleosides and their analogues have potent anti-cancer and/or anti-viral activity. Therefore, medicinal chemists continue to search for improved nucleoside synthesis techniques for condensing nucleobases and carbohydrates to form the N-glycosidic bond.

The original nucleoside glycosylation process, known as the Koenigs-Knorr procedure, is described in *Chem. Ber.*, 34, 957 (1901) and *Comprehensive Organic Chemistry*, Barton and Ollis Edition, 5, 60 (1979) and involves reacting acetobromoglucose with the silver salt of a halogenated purine to form blocked nucleosides.

Davoll and Lowy, *J. Am. Chem. Soc.*, 73, 1650 (1951), developed the first major advance in nucleoside synthesis and showed that chloromercuri-derivatives of certain purine bases provide increased nucleoside yields. Later, this concept was extended to pyrimidine bases after a reproducible procedure for preparing mercur-pyrimidine derivatives was developed. However, it was believed that little could be done to influence the relative proportion of the 1-alpha and 1-beta anomer nucleosides that were formed.

Hilbert and Johnson, *J. Am. Chem. Soc.*, 52, 2001 (1930), developed a method for preparing nucleosides based on the alkylation of alkoxypyrimidines. For example, 2,4-dimethoxy-pyrimidine was reacted with methyl iodide to form 4-methoxy-1-methyl-2(1H)-pyrimidone and after acidifying the resulting mixture, 1-methyluracil was obtained. These studies were extended to the reaction of acetobromoglucose with 2,4-diethoxypyrimidine and led to the synthesis of 1-beta-D-glucopyranosyluracil and its cytosine analogs. The first synthesis of naturally occurring cytidine, albeit in very low yields, was also carried out using the Hilbert-Johnson method; see Howard, et al., *J. Am. Chem. Soc.*, 1052 (1947). Various literature references describe how the yields obtained by the Hilbert and Johnson method may be improved significantly by varying the solvent used in the synthesis.

Prystas, et al., *Coll. Czech. Chem. Comm.*, 31, 3990 (1966), studied the effects of 5-substituted-2,4-dialkoxypyrimidines using the Hilbert and Johnson method and found that by altering the conditions of the glycosylation reaction, the proportion of each of the alpha and beta anomers that formed could be altered.

A major advance in the field of nucleoside synthesis involved the use of silylated heterocyclic nucleobase derivatives; see T. Nishimura, et al., *Chem. Pharm. Bull.*, 11, 1470 (1963) and *Chem. Pharm. Bull.*, 12, 1471 (1964). However, the yields produced using these derivatives depend on the reaction conditions since thermally unstable halogenose is employed as the carbohydrate substrate. Consequently, elevated temperatures or excessive reaction times would reduce yields.

In view of these findings, Whittenberg, *Z. Chem.*, 4, 303 (1964) and *Chem. Ber.*, 101, 1095 (1968), set out to determine the optimum glycosylation reaction conditions and found that when inert, dry, solvents (e.g., benzene or acetonitrile and molecular sieves) were used with various mercury salts, higher yields and higher proportions of beta-anomer nucleosides were obtained.

Vorbruggen, et al., *J. Org. Chem.*, 41, 2084 (1976), taught a glycosylation process wherein a peracylated deoxycarbohydrate and silylated heterocyclic nucleobases, such as a silylated pyrimidine, were reacted in 1,2-dichloroethane or acetonitrile solvent in the presence of a Friedel-Crafts catalyst such as stannic chloride, trimethylsilylperchlorate, trimethylsilyl trifluoromethanesulfonate or trimethylsilylmethane sulfonate. The reaction proceeds rapidly at room temperature which, in part, is the reason why the Vorbruggen glycosylation process has been widely accepted as the standard for nucleoside synthesis. Although the Vorbruggen process provides a higher yield of nucleosides a 1:1 alpha to beta anomer mixture of deoxy nucleoside products is obtained.

The formation of the N-glycoside bond in 2'-deoxy-2',2'-difluoronucleoside synthesis is much more difficult than in instances where the carbohydrate is 1,2-anchiomericly assisted or contains only 1 fluorine at the C-2 position. The traditional carbohydrate leaving groups, such as those used in the Vorbruggen condensation method, acetate, chloride and bromide, render the carbohydrate inactive. In order to overcome this problem, U.S. Pat. No. 4,526,988, Hertel, used a modified Vorbruggen condensation method that relies on more reactive sulfonate leaving groups to affect the reactivity of the carbohydrate. Hertel describes reacting a hydroxy protected 2-deoxy-2,2-difluoro-D-ribofuranose, containing a methanesulfonate, toluenesulfonate, ethanesulfonate, isopropanesulfonate or 4-methoxybenzenesulfonate leaving group at the C-1 position with a nucleobase derivative at temperatures of 50° C. to 220° C., in the presence of a high boiling solvent, such as dimethylformamide, dimethylacetamide and hexamethylphosphoramide. However, when the reaction is carried out at elevated pressures, any convenient inert solvent such as ethers, halogenated alkanes, and aromatics, could be used. Hertel's process requires a catalyst such as trifluoromethane-sulfonyloxysilane, at reaction temperatures from room temperature to 100° C.

U.S. Pat. No. 4,965,374, Chou, et al., states that Hertel's nucleoside product is formed in a 4:1 alpha to beta anomer ratio and goes on to describe another process based on the Vorbruggen condensation method for preparing nucleosides that employs a pivotal intermediate of 2-deoxy-2,2-difluoro-3,5-di-O-benzoyl-alpha-D-arabinosyl methanesulfonate. However, Chou forms nucleoside products in a 1:1 alpha to beta anomer ratio.

Anion glycosylation procedures have proven to be a reliable method for preparing certain substituted purine nucleosides without a fluorine substitutent at the 2' position. Robins, et al., *J. Am. Chem. Soc.*, 106, 6379–6382 (1984); for substituted pyrimidine nucleosides see Seela, et al., *Liebigs Ann. Chem.*, 895–901 (1989); and for substituted triazole nucleosides see Sanghvi, et al., *Nucleosides and*

Nucleotides, 6, 761–774 (1987); containing a 2'-deoxy-beta-D-erythro-pentofuranosyl moiety. The utility of anion coupling stems from the preparation of highly reactive 2-deoxy-3,5-di-O-(p-toluoyl)-alpha-D-erythropentofuranosyl chloride described by Hoffer in *Chem. Ber.*, 93, 2777 (1960).

The incorporation of a fluorine atom within the carbohydrate moiety of a nucleoside can substantially alter the biological properties of the nuceloside; see Fox, et al., *Carbohydry. Res.*, 42, 233 (1975), where 2-deoxy-2-fluoro-3-O-acetyl-5-O-benzoyl-alpha-D-arabinofuranosyl bromide was coupled with a heterocycle under a variety of conditions to create biologically active monofluoro-nucleosides. Howell, et al., *J. Org. Chem.*, 53, 85–88 (1988) and European Patent 0145978 disclose a simplified method for preparing monofluoro halogenose intermediates, such as 2-deoxy-2-fluoro-3, 5-O-benzoyl-alpha-D-arabinofuranosylhalogenose, amenable to large scale production. Although more reactive leaving groups were attached to the monofluoro halogenose at the C-1 position the carbohydrate intermediates continued to be less reactive with the nucleobase than their 2-deoxy counterparts.

European Patent Application 0428109 describes a process for synthesizing 2'-fluoro-2', 3'-dideoxyarabino-furanose derivatives of inosine and adenine nucleosides by coupling a monofluorosugar derivative such as 1-bromo-2-deoxy-3, 5-di-O-benzoyl-2-fluoro-α-D-arabinofuranose with the sodium salt of a purine nucleobase in solvent at temperatures from 20° C. to 90° C.

Hertel, et al., *Nucleotides and Nucleosides.*, 8, 951–955, (1989), describes a process for preparing purine nucleosides by reacting an anomeric mixture of 2-deoxy-2,2-difluoro-D-ribofuranose with a purine base, diethyl azodicarboxylate and triphenylphosphine in a solvent. However, the process provided a poor yield of nucleoside products.

Despite the preceding advances in nucleoside synthesis, there continues to be a need for an efficient stereoselective glycosylation process capable of efficiently producing alpha- or beta-anomer enriched 2'-deoxy-2',2'-difluoronucleosides and 2'-deoxy-2'-fluoronucleosides in increased yields.

Accordingly, one object of the present invention is to provide a stereoselective anion glycosylation process for preparing alpha- or beta-anomer enriched 2'-deoxy-2',2'-difluoronucleosides and 2'-deoxy-2'-fluoronucleosides without the use of a catalyst.

Another object of the present invention is to provide a stereoselective anion glycosylation process for preparing alpha- or beta-anomer enriched 2'-deoxy-2',2'-difluoronucleosides and 2'-deoxy-2'-fluoronucleosides in yields higher than those produced by conventional glycosylation procedures.

Yet another object of the present invention is to provide a stereoselective anion glycosylation process for preparing alpha- or beta-anomer enriched 2'-deoxy-2',2'-difluoronucleosides and 2'-deoxy-2'-fluoronucleosides offering a means for isolating beta- or alpha-anomer enriched nucleosides in the form of a crude product or acid addition salt such as a hydrochloride salt.

Other objects and advantages of the present invention will become apparent from the following description of embodiments.

SUMMARY OF THE INVENTION

The invention is a stereoselective anion glycosylation process for preparing a beta-anomer enriched nucleoside of the formula

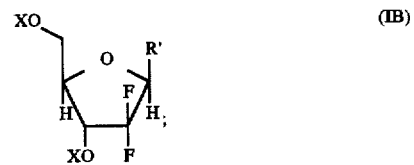

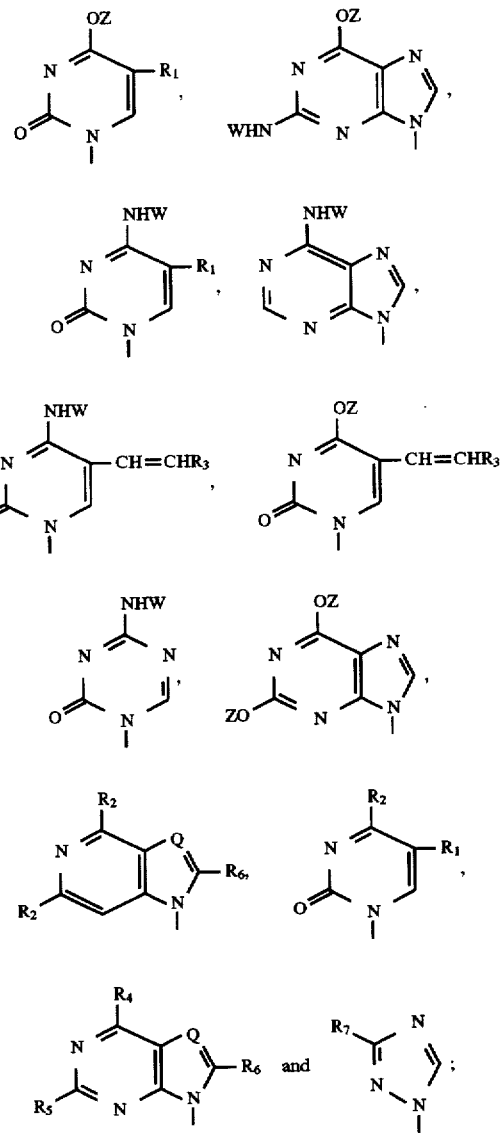

wherein each X is independently selected from hydroxy protecting groups and R' is a nucleobase selected from the group consisting of wherein R₁ is selected from the group consisting of hydrogen, alkyl, substituted alkyl and halo; R₂ is selected from the group consisting of hydroxy, halo, cyano, azido, primary amino and secondary amino; R₃ is selected from the group consisting of hydrogen, alkyl, substituted alkyl and halo; R₄, R₅ and R₆ are independently selected from the group consisting of hydrogen, —OZ, —NHW, N(alkyl)W, halo, cyano, azido, alkoxy and thioalkyl; R₇ is selected from the group consisting of hydrogen, halo, cyano, alkyl, alkoxy, alkoxycarbonyl, thioalkyl, thiocarboxamide and carboxamide; Q is selected from the group consisting of CH, CR₈ and N; wherein $R_8$ is halo, carboxamide, thiocarboxamide, alkoxycarbonyl and nitrile; Z is a hydroxy protecting group and W is an amino protecting group; comprising reacting a alpha-anomer enriched 2,2-difluorocarbohydrate of the formula

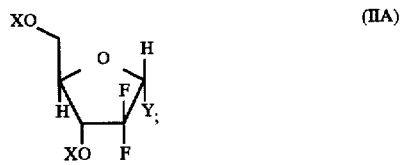
(IIA)

wherein Y is selected from the group consisting of iodo, bromo, alkylsulfonyloxy, substituted alkylsulfonyloxy, arylsulfonyloxy and substituted arylsulfonyloxy and X is as defined above; with at least a molar equivalent of a salt of a nucleobase derivative (R") selected from the group consisting of

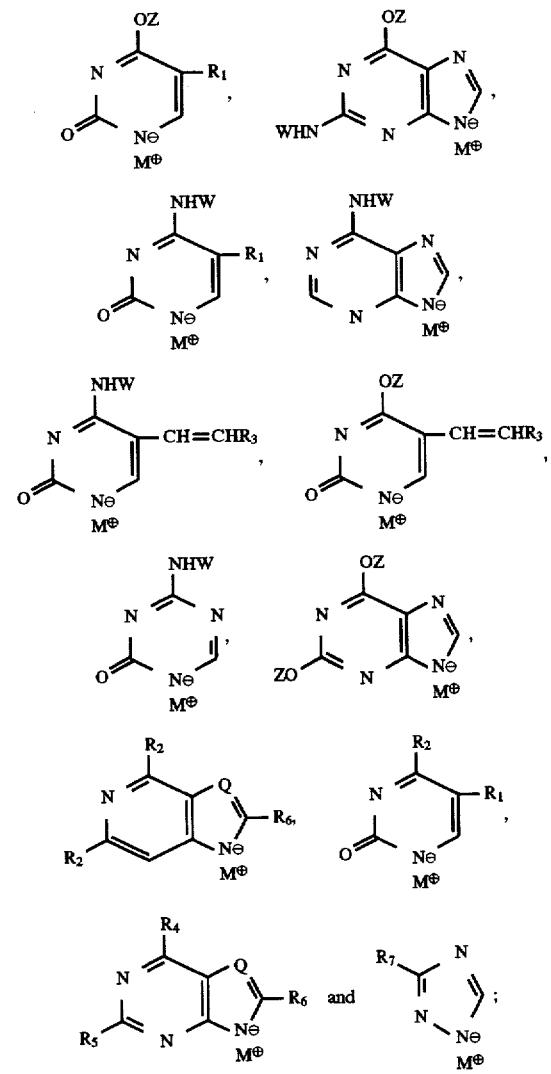

wherein $R_1$ through $R_7$, Q, Z and W are as defined above and $M^+$ is a cation; in an inert solvent.

In another aspect, the invention is a stereoselective anion glycosylation process for preparing an alpha-anomer enriched nucleoside of the formula

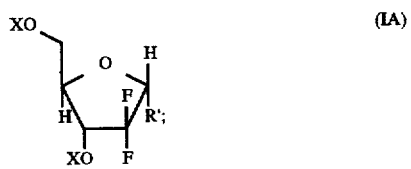
(IA)

wherein X and R' are as defined above; comprising reacting a beta-anomer enriched 2,2-difluorocarbohydrate of the formula

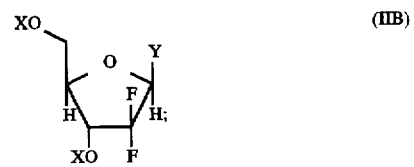
(IIB)

wherein X and Y are as defined above; with at least a molar equivalent of a cation salt of a nucleobase derivative, R", wherein R" is as defined above; in an inert solvent.

In another aspect, the invention is a stereoselective anion glycosylation process for preparing a beta-anomer enriched nucleoside of the formula

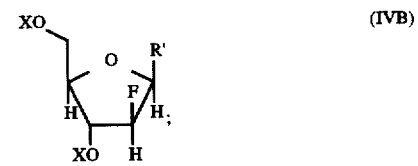
(IVB)

wherein X and R' are as defined above; comprising reacting a alpha-anomer enriched 2-fluorocarbohydrate of the formula

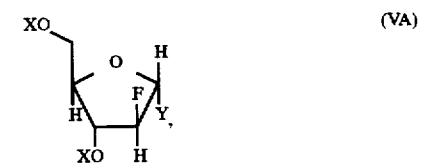
(VA)

wherein Y is selected from the group consisting of iodo, alkylsulfonyloxy, substituted alkylsulfonyloxy, substituted arylsulfonyloxy and arylsulfonyloxy and X is as defined above; with at least a molar equivalent of a cation of a nucleobase derivative, R", wherein R" is as defined above; in an inert solvent.

In another aspect, the invention is a stereoselective anion glycosylation process for preparing a alpha-anomer enriched nucleoside of the formula

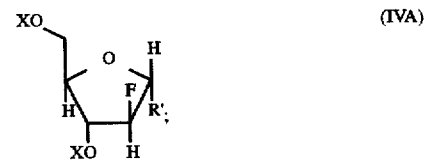
(IVA)

wherein X and R' are as defined above; comprising reacting a beta-anomer enriched 2-fluorocarbohydrate of the formula

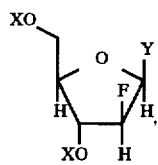

(VB)

wherein X and Y are as defined above; with at least a molar equivalent of a cation salt of a nucleobase derivative, R", wherein R" is as defined above; in an inert solvent.

The invention also provides a stereoselective anion glycosylation process for preparing a beta-anomer enriched nucleoside of the formula

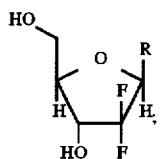

(VIB)

wherein R is a deblocked nucleobase selected from the group consisting of

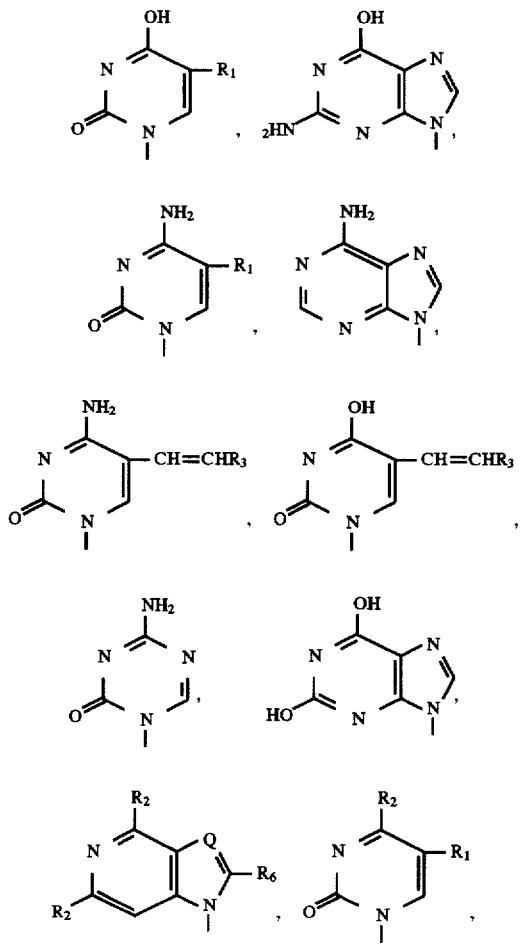

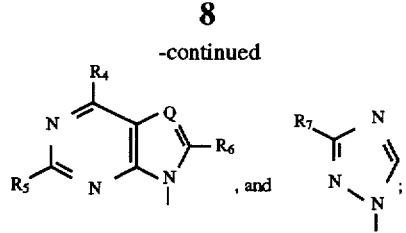

-continued

, and wherein $R_1$ is selected from the group consisting of hydrogen, alkyl, substituted alkyl and halo; $R_2$ is selected from the group consisting of hydroxy, halo, azido, primary amino and secondary amino; $R_3$ is selected from the group consisting of hydrogen, alkyl and halo; $R_4$, $R_5$ and $R_6$ are independently selected from the group consisting of hydrogen, —OH, —NH$_2$, N(alkyl)W, halo, alkoxy and thioalkyl; $R_7$ is selected from the group consisting of hydrogen, halo, cyano, alkyl, alkoxy, alkoxycarbonyl, thioalkyl, thiocarboxamide and carboxamide; Q is selected from the group consisting of CH, CR$_8$ and N; wherein R$_8$ is selected from the group consisting of halo, carboxamide, thiocarboxamide, alkoxycarbonyl and nitrile; comprising reacting an alpha-anomer enriched 2,2-difluorocarbohydrate of the formula

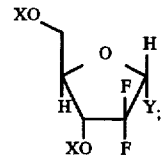

(IIA)

wherein Y is selected from the group consisting of iodo, bromo, alkylsulfonyloxy, substituted alkylsulfonyloxy, arylsulfonyloxy and substituted arylsulfonyloxy and each X is a hydroxy protecting group; with at least a molar equivalent of a salt of a nucleobase derivative (R") selected from the group consisting of

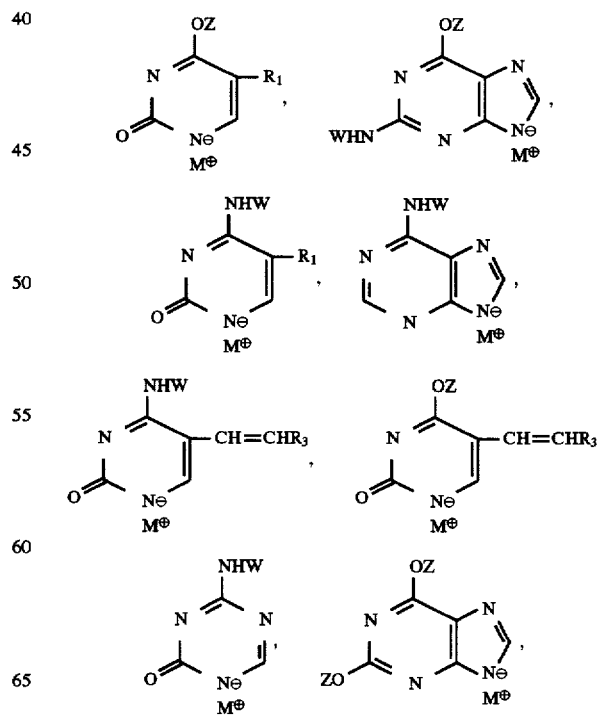

-continued

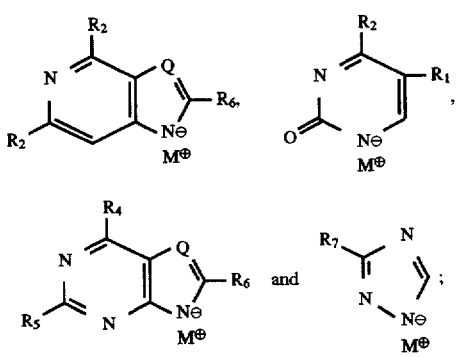

wherein R₁ through R₇ and Q are as defined above; Z is a hydroxy protecting group; W is an amino protecting group; and M⁺ is a cation; in an inert solvent; and deblocking.

Also provided is a stereoselective anion glycosylation process for preparing an alpha-anomer enriched nucleoside of the formula

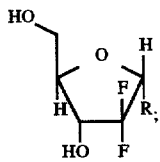
(VIA)

wherein R is a deblocked nucleobase as defined above; comprising reacting an beta-anomer enriched 2,2-difluorocarbohydrate of the formula

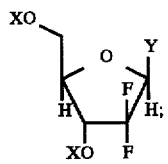
(IIB)

wherein Y and X are as defined above; with at least a molar equivalent of a salt of a nucleobase derivative (R"), wherein R" is as defined above; in an inert solvent; and deblocking.

Also provided is a stereoselective anion glycosylation process for preparing a beta-anomer enriched nucleoside of the formula

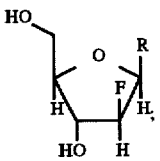
(VIIB)

wherein R is a deblocked nucleobase as defined above; comprising reacting an alpha-anomer enriched 2-fluoro carbohydrate of the formula

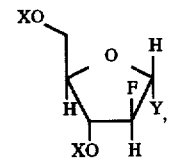
(VA)

wherein Y is selected from the group consisting of iodo, alkylsulfonyloxy, substituted alkylsulfonyloxy, arylsulfonyloxy and substituted arylsulfonyloxy and each X is a hydroxy protecting group; with at least a molar equivalent of a salt (R") of a nucleobase derivative; wherein R" is as defined above; in an inert solvent; and deblocking.

Finally, the invention provides a stereoselective anion glycosylation process for preparing an alpha-anomer enriched nucleoside of the formula

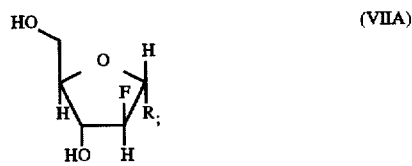
(VIIA)

wherein R is a deblocked nucleobase as defined above; comprising reacting a beta-anomer enriched 2-fluorocarbohydrate of the formula

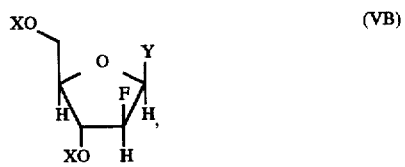
(VB)

wherein Y is selected from the group consisting of iodo, bromo, alkylsulfonyloxy, substituted alkylsulfonyloxy, arylsulfonyloxy and substituted arylsulfonyloxy and each X is a hydroxy protecting group; with at least a molar equivalent of a salt of a nucleobase derivative (R"); wherein R" is as defined above; in an inert solvent; and deblocking.

DETAILED DESCRIPTION OF THE INVENTION

Throughout this document, all temperatures are in degrees Celsius, all proportions, percentages and the like, are in weight units and all mixtures are in volume units, except where otherwise indicated. Anomeric mixtures are expressed as a weight/weight ratio or as a percent. The term "xylenes" alone or in combination refers to all isomers of xylene and mixtures thereof. The term "lactol" alone or in combination refers to a 2-deoxy-2,2-difluoro-D-ribofuranose or 2-deoxy-2-fluoro-D-ribofuranose. The term "carbohydrate" alone or in combination refers to a lactol wherein the hydroxy group at the C-1 position has been replaced by a desirable leaving group. The term "halo" alone or in combination refers to chloro, iodo, fluoro and bromo. The term "alkyl" alone or in combination refers to straight, cyclic and branched chain aliphatic hydrocarbon groups which preferably contain up to 7 carbon atoms such as methyl, ethyl, n-propyl, isopropyl, n-butyl, t-butyl, n-pentyl, n-hexyl, 3-methylpentyl groups and the like or substituted straight and branched chain aliphatic hydrocarbons such as chloroethyl, 1,2-dichloroethyl and the like. The term "alkoxy" alone or in combination refers to the general formula AO; wherein A is alkyl. The term "aryl" alone or in combination refers to carbocyclic or heterocyclic groups such as phenyl, naphthyl, thienyl and substituted derivatives thereof. The term "thioalkyl" alone or in combination refers to the general formula BS; wherein B is alkyl or hydrogen. The term "ester" alone or in combination refers to the general formula EOOC; wherein E is alkyl or aryl. The term "aromatic" alone or in combination refers to benzene like structures containing (4π+2) delocalized π electrons. The terms "sulfonate" or "sulfonyloxy" alone or in combination refer to the general formula GSO₃; wherein G is alkyl, substituted alkyl, aryl or substituted aryl. The term "substituted" alone or in combination refers to substitution by at least one or more of the groups selected from cyano, halo, carboalkoxy, toluoyl, nitro, alkoxy, hydroxy and dialkylamino. The phrase "anomer enriched" alone or in combination refers to an anomeric mixture wherein the ratio of a specified anomer is greater than 1:1 and includes a substantially pure anomer.

In accordance with the present anion glycosylation process, alpha- and beta-anomer enriched 2'-deoxy-2',2'-difluoronucleosides and 2'-deoxy-2'-fluoronucleosides of formulas IA(d), and IB(B) and IVA(d), IVB(B) are prepared by reacting an alpha- or beta-anomer enriched carbohydrate of formulas IIA(d), IIB(B) and VA(d), VB(B) with at least a molar equivalent of a nucleobase derivative anion, in an inert solvent as shown by the following reaction schemes for making beta-anomer nucleosides:

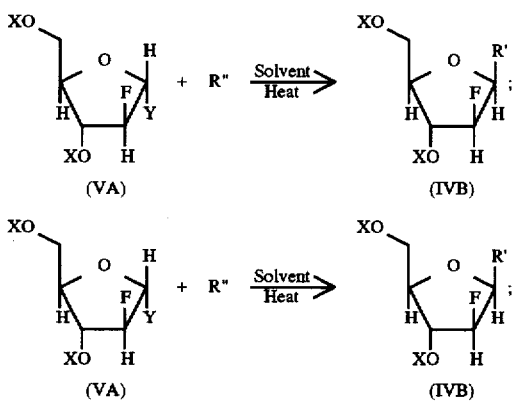

herein X, Y, R" and R' are as defined above.

While not wishing to be bound by theory, it is believed that the glycosylation reaction proceeds primarily via $S_N2$ displacement. Therefore, beta-anomer enriched nucleoside products are predominantly derived from alpha-anomer enriched carbohydrates.

The lactol starting materials suitable for use in the present glycosylation process are commonly known in the art and can be readily synthesized by standard procedures commonly employed by those of ordinary skill in the art. For example, U.S. Pat. No. 4,526,988 teaches the synthesis of 2,2-difluoro-2-deoxy-D-ribofuranoses having the formula

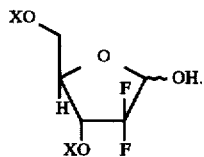 (III)

In addition, Reichman, et al., *Carbohydr. Res.*, 42, 233 (1975) teaches the synthesis of 2-deoxy-2-fluoro-D-ribofuranoses of the formula

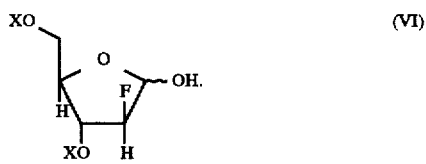 (VI)

In a preferred embodiment of the present invention, 2,2-difluoro-2-deoxy-D-ribofuranose-3,5-dibenzoate is used to prepare blocked nucleoside products.

Glycosylation reactions typically require protecting the hydroxy groups of the lactol of formulas III and VI to prevent the hydroxy groups from reacting with the nucleobase derivative, or being decomposed in some manner. Hydroxy protecting groups (X) suitable for use in the present glycosylation process may be chosen from known protecting groups used in synthetic organic chemistry. Each hydroxy protecting group selected is preferably capable of being efficiently placed on the lactol and easily removed therefrom once the glycosylation reaction is completed. Hydroxy protecting groups known in the art are described in Chapter 3 of *Protective Groups in Organic Chemistry*, McOmie Ed., Plenum Press, New York (1973), and Chapter 2 of *Protective Groups in Organic Synthesis*, Green, John, J. Wiley and Sons, New York (1981); preferred are ester forming groups such as formyl, acetyl, substituted acetyl, propionyl, butanoyl, pivaloyl, 2-chloroacetyl, benzoyl, substituted benzoyl, phenoxycarbonyl, methoxyacetyl; carbonate derivatives such as phenoxycarbonyl, ethoxycarbonyl, t-butoxycarbonyl, vinyloxycarbonyl, 2,2,2-trichloroethoxycarbonyl and benzyloxycarbonyl; alkyl ether forming groups such as benzyl, diphenylmethyl, triphenylmethyl, t-butyl, methoxymethyl, tetrahydropyranyl, allyl, tetrahydrothienyl, 2-methoxyethoxy methyl; and silyl ether forming groups such as trialkylsilyl, trimethylsilyl, isopropyldialkylsilyl, alkyldiisopropylsilyl, triisopropylsilyl, t-butyldialkylsilyl and 1,1,3,3-tetraisopropyldisiloxanyl; carbamates such as N-phenylcarbamate and N-imidazoylcarbamate; however more preferred are benzoyl, mono-substituted benzoyl and disubstituted benzoyl, acetyl, pivaloyl, triphenylmethyl ethers, and silyl ether forming groups, especially t-butyldimethylsilyl; while most preferred is benzoyl.

In attaching each hydroxy protecting group to the lactol, typical reaction conditions are employed and depend on the nature of the protecting group chosen. Suitable reaction conditions are discussed in U.S. Pat. No. 4,526,988 which is incorporated herein by reference.

To obtain an efficient reaction of the nucleobase derivative and carbohydrate, an appropriate leaving group is stereoselectively attached to the lactol at the C-1 position which activates the lactol and generates the beta- and alpha-anomer enriched carbohydrate of formulas II and V. Suitable leaving groups (Y) are selected from the group consisting of iodo, bromo, alkylsulfonyloxy, substituted alkylsulfonyloxy, arylsulfonyloxy and substituted arylsulfonyloxy; more preferred are p-bromo benzenesulfonyloxy, p-nitrobenzenesulfonyloxy, iodo and bromo; while most preferred is iodo.

The alpha-anomer enriched carbohydrate of formula II may be prepared by one of three methods. The alpha-anomer enriched carbohydrate of formula V is prepared by the second of these methods. The first method, described in pending U.S. Pat. No. 5,256,798, teaches treating a beta-anomer ribofuranosyl sulfonate or anomeric mixture thereof with a source of a conjugate anion of a sulfonic acid at elevated temperatures in an inert solvent. The second method is described in pending U.S. Pat. No. 5,401,861, and teaches reacting the lactol of formulas III and VI with an amine base such as triethylamine, tributylamine, dibutylamine, diethylmethylamine, dimethylethylamine, benzylmethylamine, N-methylmorpholine, tripropylamine, dipropylethylamine, N, N-dimethylbenzylamine, diisopropylethylamine, diethylamine, 1,8-diazabicyclo[5.4.0]undec-7-ene and 1,5-diazabicyclo[4.3.0]non-5-ene. The amine base preferably has a pKa of from about 8 to about 20 and is employed in a range of from about 1 molar equivalent to about 2 molar equivalents and more preferably from about 1.2 molar equivalents to about 1.5 molar equivalents. The reaction is carried out in an inert solvent having a freezing point temperature preferably below -78° C.

Preferred solvents are selected from the group consisting of dichloromethane, 1,2-dichloroethane, dichlorofluoromethane, acetone, toluene, anisole, chlorobenzene, and mixtures thereof. The temperature of the solvent mixture is adjusted preferably in the range from about −40° C. to about −20° C. and more preferably below about −78° C. While not wishing to be bound by theory it is believed that the low temperature shifts the alpha to beta anomeric ratio of the lactol in favor of the alpha-anomer in a range from about 2:1 to about 4:1 alpha to beta. For example, a compound of formula III, where X is benzoyl, was added to dichloromethane and triethylamine at room temperature for 30 minutes. Next, the temperature of the solvent mixture was lowered. An $^{19}$F NMR, taken at various temperatures showed an increase in the alpha to beta ratio of the ionized lactol as the temperature was lowered:

| Temperature | Alpha/Beta Ratio |
|---|---|
| 19° C. | 2.0:1 |
| −3° C. | 2.3:1 |
| −23° C. | 2.5:1 |
| −43° C. | 3.0:1 |
| −63° C. | 3.6:1 |
| −83° C. | 4.4:1 |

The ionized lactol is then trapped in solution at the low temperature and higher alpha-anomer ratio by adding a sulfonating reagent which forms an alpha-anomer enriched carbohydrate. The third method, described in pending U.S. patent application Ser. No. 07/902,306, Attorney Docket X-7775, teaches a stereoselective process for preparing alpha-anomer enriched 1-α-halo-2-deoxy-2,2-difluoro-D-ribofuranosyl derivatives involving contacting a hydroxy protected 2-deoxy-2,2-difluoro-D-ribofuranosyl-1-β-sulfonate with a halide source in an inert solvent.

The sulfonating reagents are selected from the group consisting of substituted and unsubstituted aryl- and alkyl-sulfonyl halides, such as methanesulfonyl chloride, and aryl- and alkyl-sulfonic acid anhydrides, depending on the leaving group desired.

A method for preparing the beta-anomer enriched carbohydrates of formulas II and V are described in pending U.S. Pat. No. 5,252,756. The method requires reacting the lactol of formulas III and VI with an arylsulfonyl halide, substituted arylsulfonyl halide, arylsulfonic anhydride, or substituted arylsulfonic anhydride such as toluenesulfonyl chloride, benzenesulfonyl chloride o-nitrobenzenesulfonyl chloride, p-nitrobenzenesulfonyl chloride, 2,4-dinitrobenzenesulfonyl chloride and p-bromobenzenesulfonyl chloride in the presence of an amine base such as triethylamine.

The beta- or alpha-anomer enriched 2-deoxy-2,2-difluoro-D-ribofuranosyl-1-alkylsulfonates may be isolated in substantially pure form; i.e., greater than 95 percent purity; by the procedure described in Pending U.S. Pat. No. 5,256,797. The method involves warming an anomeric mixture of the alkylsulfonates in a solvent from about 30° C. to about 70° C. to form a supersaturated solution. The solvent may be selected from the group consisting of 1,2-dichloroethane, anisole, glyme, and mixtures thereof. The carbohydrate forms as a precipitate when the temperature of the solution is lowered and a counter solvent is added. The counter solvent may be selected from the group consisting of methanol, ethanol, toluene, ether, dichloromethane, and mixtures thereof. The resulting carbohydrate crystals are then recovered from the solution and dried.

The nucleobases (R") employed herein are commonly known to organic chemist and no discussion of their synthesis is necessary. However, in order to be useful in the present glycosylation process the nucleobase derivatives or their tautomeric equivalents bearing amino or hydroxy groups preferably contain protecting groups such as amino protecting groups (W) and/or hydroxy protecting groups (Z), depending on the nature of the nucleobase derivative selected. The protecting group blocks the hydroxy or amino groups which may provide a competing reaction site for the beta- or alpha-anomer carbohydrate. The protecting groups are attached to the nucleobase derivative (R') before it is reacted with the beta- or alpha-anomer enriched carbohydrate of formulas II and V and are removable subsequent thereto. A procedure for protecting nucleobase derivatives is described in U.S. Pat. No. 4,526,988.

Preferred amino protecting groups (W) for pyrimidine nucleobase derivatives are selected from the group consisting of silyl ether protecting groups such as trialkylsilyl, t-butyldialkylsilyl and t-butyldiarylsilyl; carbamates such as t-butoxycarbonyl, benzyloxycarbonyl, 4-methoxybenzyloxycarbonyl, and 4-nitrobenzyloxycarbonyl; formyl, acetyl, benzoyl and pivaloyl; ether forming groups such as methoxymethyl, t-butyl, benzyl, allyl and tetrahydropyranyl; more preferred is trimethylsilyl. Preferred amino protecting groups (W) for purine nucleobase derivatives are selected from the group consisting of alkylcarbonyls, haloalkylcarbonyls and arylcarbonyls such as pivaloyl, trifluoroacetyl, naphthoyl, formyl and acetyl. Other suitable amino protecting groups are 2-trialkylsilylethoxymethyl, 4-methoxybenzyl, 3,4-dimethoxybenzyl, t-butyl, phthalimido, tetrahydropyranyl, tetrahydrofuranyl, methoxymethyl ether, methoxythiomethyl, trityl, t-butyldimethylsilyl, t-hexyldimethylsilyl, triisopropylsilyl, trichloroethoxycarbonyl, and sulfonyls such as alkylsulfonyls and arylsulfonyls. The more preferred amino protecting group is pivaloyl. Besides serving as an amino protecting group, the pivaloyl protecting group increases the solubility of notoriously insoluble purine nucleobase derivatives and directs the N-glycosidic coupling of the purine bases to the 9 regioisomer as opposed to the 7 regioisomer.

Preferred hydroxy protecting groups (Z) for pyrimidine nucleobase derivatives are selected from silyl ether forming groups such as trialkylsilyl; carbamates such as t-butoxycarbonyl, benzyloxycarbonyl, 4-methoxybenzyloxycarbonyl and 4-nitrobenzyloxycarbonyl; carbocyclic esters such as formyl, acetyl, and pivaloyl; preferred is trimethylsilyl. Preferred hydroxy protecting groups (Z) for purine nucleobase derivatives are selected from the group consisting of ether forming groups such as benzyl, t-butyl, trityl, tetrahydropyranyl, tetrahydrofuranyl, methoxymethyl, ester-forming groups such as formyl, acetylpropionyl, pivaloyl, benzoyl, substituted benzoyl; carbonates such as carbobenzoxy, t-butoxycarbonyl, carbethoxy, vinyloxycarbonyl; carbamates, such as N,N-dialkylcarbamoyl; trialkyl-silyl ethers such as t-butyltrimethylsilyl, t-hexyldimethylsilyl, triisopropylsilyl; more preferred is pivaloyl.

In providing protecting groups to the nucleobase derivatives of the present process, the protecting group itself may be protected.

In addition, it is often advisable to convert any keto oxygen atoms on the nucleobase derivative to a protected enol form. This makes the nucleobase derivative more nucleophilic and enhances the reactivity of the nucleobase derivative with the alpha-anomer enriched carbohydrate of formulas II and V. It is most convenient to enolize the keto oxygens and provide silyl protecting groups for them.

The nucleobase derivatives employed in the present process are converted to anions to further enhance the reactivity of the nucleobase derivative with the anomer enriched carbohydrate of formulas II and V. The anion formation involves adding a base to the nucleobase derivative in a solvent. The base may be selected from the group consisting of sodium t-butoxide, potassium hydroxide, potassium-t-butoxide, potassium ethoxide, potassium methoxide, sodium ethoxide, sodium methoxide, sodium hydride, lithium hydride and potassium hydride. Alternatively the base may be selected from trialkylamine or tetraalkylammonium. The solvent may be selected from the group consisting of acetonitrile, dimethylformamide, dimethylacetamide, 1,3-dimethyl-2-imidazolidinone, N-methylpyrrolidinone, sulfolane, dimethylsulfoxide, and mixtures thereof. The solvent used to prepare the anionic nucleobase derivative may be removed prior to the glycosylation reaction or admixed with the reaction solvent, provided the admixture is inert to the glycosylation reaction.

The reaction solvents suitable for use in the present glycosylation process must be inert to the glycosylation reaction conditions. Preferred reaction solvents are selected from the group consisting of dichloromethane, 1,2-dichloroethane, dichlorofluoromethane, acetone, toluene, anisole, chlorobenzene, dimethylformamide, acetonitrile, N,N-dimethylacetamide, methanol, tetrahydrofuran, ethyl acetate, dimethoxymethane, 1,2-dimethoxyethane, dimethylsulfoxide, and mixtures thereof.

In accordance with the present process, at least an equimolar amount of nucleobase derivative (R") is employed, relative to the amount of carbohydrate employed. However, it is more preferable to use an excess of nucleobase derivative in an amount greater than 1 equivalent to about 10 equivalents and more preferably from about 2 equivalents to about 4 equivalents.

The glycosylation reaction temperature employed in the present process is from about 23° C. to about 170° C.; more preferably from about 23° C. to about 130° C., and most preferably about 23° C. to about 50° C. The glycosylation reaction is preferably carried out under atmospheric conditions and is substantially complete in about 5 minutes to about 6 hours.

Although not critical, it is advisiable that the reaction between the beta- and alpha-enriched carbohydrate of formulas II and V and the nucleobase deriviative be carried out in a dry atmosphere, e.g. in the presence of dry air, nitrogen, or argon. This is because certain nucleobase derivatives are moisture sensitive.

The progress of the present glycosylation process may be followed by procedures well known to one of ordinary skill in the art such as high pressure liquid chromatography (HPLC) and thin layer chromatography (TLC) which can be used to detect the presence of nucleoside product.

In accordance with the present glycosylation process, the beta-anomer enriched nucleosides are prepared in a beta to alpha anomeric ratio of greater than 1:1 to about 10:1. On the other hand, alpha-anomer enriched nucleosides are prepared in an alpha to beta anomeric ratio of greater than 1:1 to about 20:1.

The final phase of the reaction sequence is the removal of the protecting groups X, Z and/or W from the blocked nucleoside of formula I or IV. The same anomeric ratio of unprotected nucleoside is obtained by removal of the protecting groups.

Most silyl and silyl-amino protecting groups are easily cleaved by use of a protic solvent, such as water or an alcohol. The acyl protecting groups, such as benzoyl and the acyl-amino protecting groups, are removed by hydrolysis with a strong base at a temperature from about 0° C. to about 100° C. Strong or moderately strong bases suitable for use in this reaction are bases which have a pKa (at 25° C.) of about 8.5 to about 20.0. Such bases include alkali metal hydroxides such as sodium or potassium hydroxide; alkali metal alkoxides such as sodium methoxide or potassium t-butoxide; alkali metal amides; amines such as diethylamine, hydroxylamine, ammonia and the like; and other common bases such as hydrazine and the like. At least one equivalent of base is needed for each protecting group.

The acyl protecting groups can also be removed with acid catalysts, such as methanesulfonic acid, hydrochloric acid, hydrobromic acid, sulfuric acid, or with acidic ion exchange resins. It is preferred to carry out such hydrolysis at relatively high temperature, such as the reflux temperature of the mixture, but temperatures as low as ambient may be used when particularly strong acids are used.

The removal of ether protecting groups is carried out by known methods, for example, with ethanethiol and aluminum chloride.

The t-butyldimethylsilyl protecting group requires acid conditions, such as contact with gaseous hydrogen halide, for its removal.

Removal of the protecting groups may be conveniently carried out in alcoholic solvents, especially aqueous alkanols such as methanol. However, the deblocking reaction may also be carried out in any convenient solvent, such as polyols including ethylene glycol, ethers such as tetrahydrofuran, ketones such as acetone and methyl ethyl ketone, or dimethylsulfoxide.

In a preferred embodiment, the deblocking reaction employs ammonia to remove a benzoyl hydroxy-protecting group at a temperature of about 10° C. It is preferable, however, to use an excess of base in this reaction, although the amount of excess base used is not crucial.

The resulting beta- and alpha-anomer enriched nucleosides of formulas VI and VII may be extracted and/or isolated from the reaction mixture by the procedure described in U.S. Pat. No. 4,965,374, Chou, which is incorporated herein by reference, or by conventional methods known in the art such as extraction, crystallization, etc.

The following examples illustrate specific aspects of the present invention and are not intended to limit the scope thereof in any respect and should not be so construed.

EXAMPLE 1

Preparation of (9) regioisomer-alpha-anomer enriched 1-(2'-deoxy-2', 2'-difluoro-3',5'-di-O-benzoyl-D-ribofuranosyl)-2, 6-dipivalamidopurine in acetonitrile 2,6-dipivalamidopurine (0.159 g, 0.5 mmol) was suspended in acetonitrile (1.5 ml) and treated with potassium t-butoxide (0.062 mg, 0.55 mmol) and stirred for 10 minutes under a nitrogen atmosphere at 25° C. to form the potassium salt of 2,6-dipivalamidopurine.

2-deoxy-2,2-difluoro-D-ribofuranosyl-3, 5-dibenzoyl-1-β-(p-bromobenzene)sulfonate (0.299 g, 0.5 mmol), in acetonitrile (1.5 ml), was added to the above salt and the entire mixture was reacted for 20 hours at 60° C. to form a blocked nucleoside. HPLC analysis confirmed completion of the reaction and indicated an alpha to beta anomeric ratio of 10:1 of the titled product.

To isolate the nucleoside product, the solvent was removed under vacuum, diluted with ethyl acetate, washed with sodiumbicarbonate and dried over magnesium sulfate. Column chromatography (silica gel, toluene/ethyl acetate

17

1:1) gave 0.211 g of the titled product at a yield of 62 percent. MS(FD) 679 (M+1) Elemental Analysis for $C_{34}H_{36}F_2N_6O_7$: (Theoretical) C, 60.17; H, 5.35; N, 12.38; (Empirical) C, 59.77; H, 5.22; N; 11.76; m.p. 165° C.–167° C.

EXAMPLE 2

Preparation of beta-anomer enriched 1-(2'-deoxy-2',2'-difluoro-3', 5'-di-O-benzoyl-D-ribofuranosyl)-4-pivalamidopyrimid-2-one in acetonitrile N-pivaloyl cytosine (1.0 g, 5.5 mmol) was suspended in acetonitrile (15.0 ml) and treated with potassium t-butoxide (0.062 g, 5.5 mmol) and stirred under a nitrogen atmosphere at 25° C. to form the potassium salt of N-pivaloyl cytosine.

2-deoxy-2,2-difluoro-D-ribofuranosyl-3,5-dibenzoyl-1-α-(p-bromobenzene) sulfonate (2.99 g, 5.0 mmol), in acetonitrile (10.0 ml), was added to the above salt and the entire mixture was reacted for 5.5 hours at 65° C. to form a blocked nucleoside. HPLC analysis confirmed completion of the reaction and indicated a beta to alpha anomeric ratio of 3.9:1.

To isolate the nucleoside product, the reaction mixture was distributed between with ethyl acetate and water and the organic layer was washed with sodium bicarbonate and dried over magnesium sulfate. Column chromatography (silica gel, toluene/ethyl acetate 6:4) gave 0.700 g of the titled product at a yield of 20 percent; m.p. 191° C.–193° C.

EXAMPLE 3

Preparation of beta-anomer enriched 1-(2'-deoxy-2',2'-difluoro-3', 5'-di-O-benzoyl-D-ribofuranosyl)-4-(N-pivalamidopyrmid-2-one in acetonitrile N-pivaloylcytosine (0.098 g, 0.5 mmol) was suspended in acetonitrile (1.5 ml) and treated with potassium t-butoxide (0.062 g, 0.55 mmol) and stirred under a nitrogen atmosphere at 25° C. to form the potassium salt of N-pivaloylcytosine.

2-deoxy-2,2-difluoro-D-ribofuranosyl-3,5-dibenzoyl-1-α-iodide (0.244 g, 0.5 mmol), in acetonitrile (1.5 ml), was added to the above salt and the entire mixture was reacted for 24 hours at 60° C. to form a blocked nucleoside. HPLC analysis confirmed completion of the reaction and indicated a beta to alpha anomeric ratio of 1.13:1.

EXAMPLE 4

Preparation of beta-anomer enriched 1-(2'-deoxy-2', 2'-difluoro-3',5'-di-O-benzoyl-D-ribofuranosyl)-1,2,4-triazole-3-carbonitrile in acetonitrile 1,2,4-triazole-3-carbonitrile (0.101 g, 1.03 mmol) was suspended in acetonitrile (10 ml) and treated with sodium hydride (0.0445 g, 1.12 mmol) and stirred under a nitrogen atmosphere at 25° C. to form the corresponding sodium salt of the triazole. 2-deoxy-2,2-difluoro-D-ribofuranosyl-3, 5-dibenzoyl-1-α-bromide (0.451 g, 1.02 mmol), in acetonitrile (10 ml), was added to the above salt and the entire mixture was reacted for 78 hours at 82° C. to form a blocked nucleoside. HPLC analysis confirmed completion of the reaction and indicated a beta to alpha anomeric ratio of 1.2:1.

To isolate the nucleoside product, the reaction mixture was evaporated to from an oily solid, diluted with ethyl acetate, washed with sodium bicarbonate and dried over magnesium sulfate and concentrated. The residue crystallized from ethanol to give 30 mg of a titled product at a yield of 6 percent; m.p. 225° C.–226° C. MS(FD) M/Z 455 (M+1) Elemental Analysis for $C_{22}H_{16}F_2N_4O_5$: (Theoretical) C, 58.15; H, 3.55; N, 12.33; (Empirical) C, 58.36; H, 3.79; N, 12.10.

EXAMPLE 5

Preparation of beta-anomer enriched 1-(2'-deoxy-2', 2'-difluoro-3',5'-di-O-benzoyl-D-ribofuranosyl)-1,2,4-triazole-3-carbonitrile in acetonitrile 1,2,4-triazole-3-carbonitrile (0.272 g, 2.89 mmol) was suspended in acetonitrile (20 ml), treated with sodium hydride (0.094 g, 2.7 mmol) and stirred under a nitrogen atmosphere at 25° C. to form the sodium salt of the triazole.

2-deoxy-2,2-difluoro-D-ribofuranosyl-3, 5-dibenzoyl-1-α-iodide (0.941 g, 1.9 mmol), in acetonitrile (20 ml), was added to the above salt and the entire mixture was reacted for 48 hours at 82° C. to form a blocked nucleoside. HPLC analysis confirmed completion of the reaction and indicated a beta to alpha anomeric ratio of 3.5:1.

To isolate the nucleoside product, the reaction mixture was evaporated to from an oily solid, diluted with ethyl acetate, washed with sodium bicarbonate, dried over magnesium sulfate and concentrated. The residue crystallized from ethanol to give 0.421 g of the titled product; m.p. 225° C.–226° C. at a yield of 48 percent. MS(FD) M/Z 455 (M+1) Elemental Analysis for $C_{22}H_{16}F_2N_4O_5$: (Theoretical) C, 58.15; H, 3.55; N, 12.33; (Empirical) C, 58.35; H, 3.65; N, 12.33.

EXAMPLE 6

Preparation of (9) regioisomer-beta-anomer enriched 1-(2'-deoxy-2',2'-difluoro-3', 5'-di-O-benzoyl-D-ribofuranosyl)-6-cyanopurine in N,N-dimethylacetamide 6-cyanopurine (0.92 g, 6.35 mmol) was suspended in N,N-dimethylacetamide (12 ml) and treated with sodium hydride (0.396 g, 8.25 mmol) and stirred under a nitrogen atmosphere at 25° C. to form the sodium salt of 6-cyanopurine.

2-deoxy-2,2-difluoro-D-ribofuranosyl-3, 5-dibenzoyl-1-α-iodide (3.09 g, 6.35 mmol), in N,N-dimethylacetamide (4 ml), was added to the above salt and the entire mixture was reacted for 5 hours at 70° C. to form a blocked nucleoside. HPLC analysis confirmed completion of the reaction and indicated a beta to alpha anomeric ratio of 1.2:1.

To isolate the nucleoside product, the reaction mixture was cooled, the solvent removed under vacuum, the residue was dissolved in ethyl acetate, washed with a 0.2 M lithium chloride solution, dried over magnesium sulfate and concentrated. Column chromatography (silica gel, toluene/ethyl acetate 9:1) gave 0.21 g of the titled product at a yield of 6.5 percent. MS(FD) 506 (M+1) Elemental Analysis for $C_{25}H_{17}F_2N_5O_5$: (Theoretical) C, 59.41; H, 3.39; N, 13.86; (Empirical) C, 59.85; H, 3.49; N, 13.48.

EXAMPLE 7

Preparation of alpha-anomer enriched 1-(2'-deoxy-2', 2'-difluoro-3',5'-di-O-benzoyl-D-ribofuranosyl)-4-(acetylamino) pyramid-2-one in N,N-dimethylacetamide N-acetylcytosine (0.306 g, 2.0 mmol) was suspended in N,N-dimethylacetamide (2.5 ml) and treated with sodium hydride (0.0264 g, 1.1 mmol) and stirred under a nitrogen atmosphere at 25° C. to form the sodium salt of N-acetylcytosine.

2-deoxy-2,2-difluoro-D-ribofuranosyl-3, 5-dibenzoyl-1-β-(p-bromobenzene)sulfonate (0.597 g, 1.0 mmol), in N,N- dimethylacetamide (2.5 ml), was added to the above salt and the entire mixture was reacted for 3.5 hours at 23° C. to form a blocked nucleoside. HPLC analysis confirmed completion of the reaction and indicated a alpha to beta anomeric ratio of at least 10:1.

To isolate the nucleoside product, the reaction mixture was allowed to cool, the solvent removed under vacuum, diluted with ethyl acetate and filtered. The filtrate was washed with sodium bicarbonate, dried over magnesium sulfate and concentrated to an oil. Column chromatography (silica gel, toluene) gave 0.045 g of the titled product at a yield of 8.7 percent. MS(FD) 514 (M+1)

EXAMPLE 8

Preparation of alpha-anomer enriched 1-(2'-deoxy-2', 2'-difluoro-3',5'-di-O-benzoyl-D-ribofuranosyl)-2,6-diazidopurine in N,N-dimethylacetamide 2,6-diazidopurine (0.299 g, 0.5 mmol) was suspended in N,N-dimethylacetamide (1.0 ml) and treated with potassium t-butoxide (0.059 g, 0.525 mmol) and stirred under a nitrogen atmosphere at 25° C. to form the potassium salt of 2,6-diazidopurine.

2-deoxy-2,2-difluoro-D-ribofuranosyl-3, 5-dibenzoyl-1-β-(p-bromobenzene)sulfonate (0.299 g, 0.5 mmol), in N,N-dimethylacetamide (1.0 ml), was added to the above salt and the entire mixture was reacted for 17 hours at 50° C. to form a blocked nucleoside. HPLC analysis confirmed completion of the reaction and indicated an alpha to beta anomeric ratio of 10:1.

To isolate the nucleoside product, the reaction mixture was cooled, the solvent removed under vacuum, diluted with ethyl acetate, washed with sodium bicarbonate and dried over magnesium sulfate. Column chromatography (silica gel, toluene/ethyl acetate 4:1) gave 0.011 g the titled product at a yield of 4 percent. MS(FD) 563 (M+1).

EXAMPLE 9

Preparation of alpha-anomer enriched 1-(2'-deoxy-2', 2'-difluoro-3',5'-di-O-benzoyl-D-ribofuranosyl)-2, 6-dichloropurine in N,N-dimethylacetamide 2,6-dichloropurine (0.099 g, 0.525 mmol) was suspended in N,N-dimethylacetamide (1.0 ml) and treated with potassium t-butoxide (0.059 g, 0.525 mmol) and reacted under a nitrogen atmosphere at 25° C. to form the potassium salt of 2,6-dichloropurine.

2-deoxy-2,2-difluoro-D-ribofuranosyl-3, 5-dibenzoyl-1-β-(p-bromobenzene)sulfonate (0.299 g, 0.5 mmol), in N,N-dimethylacetamide (1.0 ml), was added to the above salt and the entire mixture was stirred for 4 hours at 55° C. to form a blocked nucleoside. HPLC analysis confirmed completion of the reaction and indicated an alpha to beta anomeric ratio of at least 10:1.

To isolate the nucleoside product, the reaction mixture was cooled, the solvent removed under vacuum. The residue was diluted with ethyl acetate, washed with sodium bicarbonate, dried over magnesium sulfate and concentrated to an oil. Column chromatography (silica gel, toluene/ethyl acetate 9:1) gave 0.043 g of the titled product at a yield of 15.5 percent. MS(FD) 547 (M+1).

EXAMPLE 10

Preparation of (9) regioisomer-beta-anomer enriched 1-(2'-deoxy-2',2'-difluoro-3', 5'-di-O-benzoyl-D-ribofuranosyl)-2,6-dipivalamidopurine in N,N-dimethylacetamide 2,6-dipivalamidopurine (0.159 g, 0.5 mmol) was suspended in N,N-dimethylacetamide (1.0 ml) and treated with potassium t-butoxide (0.062 g, 0.55 mmol) and stirred under a nitrogen atmosphere at 25° C. to form the potassium salt of 2,6-dipivalopurine.

2-deoxy-2,2-difluoro-D-ribofuranosyl-3, 5-dibenzoyl-1-α-(p-bromobenzene) sulfonate (0.299 g, 0.5 mmol), in N,N-dimethylacetamide (0.5 ml), was added to the above salt and the entire mixture was reacted for 6 hours at 60° C. to form a blocked nucleoside. HPLC analysis confirmed completion of the reaction and indicated a beta to alpha anomeric ratio of 1.9:1 of the titled product.

To isolate the nucleoside product, the reaction mixture was cooled and the solvent removed under vacuum. The residue was diluted with ethyl acetate, washed with sodium bicarbonate, dried over magnesium sulfate and concentrated to an oil. Column chromatography (silica gel, toluene/ethyl acetate 1:1) gave 0.141 g of both alpha and beta nucleoside products at a yield of 28 percent. MS(FD) 679 (M+1).

EXAMPLE 11

Preparation of (9) regioisomer-beta-anomer enriched 1-(2'-deoxy-2',2'-difluoro-3', 5'-di-O-benzoyl-D-ribofuranosyl)-2,6-dipivalamidopurine in acetonitrile 2,6-dipivalamidopurine (0.159 g, 0.5 mmol) was suspended in acetonitrile (1.5 ml) and treated with potassium t-butoxide (0.062 g, 0.55 mmol) and stirred under a nitrogen atmosphere at 25° C. to form the potassium salt of 2,6-dipivalamidpurine.

2-deoxy-2,2-difluoro-D-ribofuranosyl-3, 5-dibenzoyl-1-α-iodide (0.244 g, 0.5 mmol), in acetonitrile (1.5 ml), was added to the above salt and the entire mixture was reacted for 16 hours at 60° C. to form a blocked nucleoside. HPLC analysis confirmed completion of the reaction and indicated a beta to alpha anomeric ratio of 2.2:1.

To isolate the nucleoside product, the reaction mixture was diluted with ethyl acetate, the organic layer was washed with sodium bicarbonate, dried over magnesium sulfate separated and concentrated to an oil. Column chromatography (silica gel, toluene/ethyl acetate 1:1) followed by recrystallization gave 0.085 g of the titled product at a yield of 25 percent. MS(FD) 679 (M+1).

EXAMPLE 12

Preparation of alpha-anomer enriched ethyl 1-(2'-deoxy-2', 2'-difluoro-3',5'-di-O-benzoyl-D-ribofuranosyl)-1, 2,4-triazole-3-carboxylate in N,N-dimethylacetamide Ethyl 1,2,4-triazole-3-carboxylate (0.355 g, 2.51 mmol) was suspended in N,N-dimethylacetamide (2.5 ml), treated with sodium hydride (0.06 g, 2.5 mmol) and stirred under a nitrogen atmosphere at 25° C. to form the sodium salt of ethyl 1,2,4-triazole-3-carboxylate.

2-deoxy-2,2-difluoro-D-ribofuranosyl-3, 5-dibenzoyl-1-β-(p-bromobenzene) sulfonate (1.0 g, 1.68 mmol), in N,N-dimethylacetamide (2.5 ml), was added to the above salt and the entire mixture was reacted for 22 hours at 25° C. to form a blocked nucleoside. HPLC analysis confirmed completion of the reaction and indicated an alpha to beta anomeric ratio of 10:1.

The crude reaction mixture was purified by column chromatography (silica gel, toluene/ethyl acetate 9:1) gave 0.196 g of the titled product at a yield of 25 percent. MS(FD) M/Z 501 (M+1).

EXAMPLE 13

Preparation of beta-anomer enriched 1-(2'-deoxy-2',2'-difluoro-3', 5'-di-O-benzoyl-D-ribofuranosyl)-4-(benzylamino) pyramid-2-one in N,N-dimethylacetamide N-benzylcytosine (0.099 g, 0.493 mmol) was suspended in N,N-dimethylacetamide (2.0 ml) and treated with sodium hydride (0.0256 g, 0.534 mmol) and stirred under a nitrogen atmosphere at 25° C. to form the sodium salt of N-benzylcytosine.

2-deoxy-2,2-difluoro-D-ribofuranosyl-3, 5-dibenzoyl-1-α-iodide (0.201 g, 0.411 mmol), in N,N-dimethylacetamide (1.5 ml), was added to the above salt and the entire mixture was reacted for 5 hours at 23° C. to form a blocked nucleoside. HPLC analysis confirmed completion of the reaction and indicated a beta to alpha anomeric ratio of 1.9:1.

The reaction solvents were removed under vacuum and the residue was dissolved in ethyl acetate, washed with sodium bicarbonate, dried over magnesium sulfate and concentrated to an oil. Column chromatography (silica gel, toluene/ethyl acetate 9:1) gave 0.015 mg of the titled product at a yield of 6.5 percent. MS(FD) 562 (M+2).

EXAMPLE 14

Preparation of beta-anomer enriched ethyl 1-(2'-deoxy-2', 2'-difluoro-3', 5'-di-O-benzoyl-D-ribofuranosyl)-1,2, 4-triazole-3-carboxylate in N,N-dimethylacetamide Ethyl 1,2,4-triazole-3-carboxylate (0.723 g, 5.13 mmol) was suspended in N,N-dimethylacetamide (2.5 ml), treated with sodium hydride (0.123 g, 5.13 mmol) and stirred under a nitrogen atmosphere at 25° C. to form the sodium salt of the triazole.

2-deoxy-2,2-difluoro-D-ribofuranosyl-3, 5-dibenzoyl-1-α-iodide (2.0 g, 4.11 mmol), in N,N-dimethylacetamide (2.5 ml), was added to the above salt and the entire mixture was reacted for 24 hours at 23° C. to form a blocked nucleoside. HPLC analysis confirmed completion of the reaction and indicated a beta to alpha anomeric ratio of 3:1.

The crude reaction mixture was purified by removing the solvent under reduced pressure and employing column chromatography (silica gel, toluene/ethyl acetate 9:1). The combined theoretical yield of alpha and beta regioisomers (A and B below) of blocked nucleosides was 67 percent.

A. Ethyl 1-(2'-deoxy-2', 2'-difluoro-3',5'-di-O-benzoyl-β-D-ribofuranosyl) -1,2,4-triazole-3-carboxylate (436 mg, 21.2 percent yield).

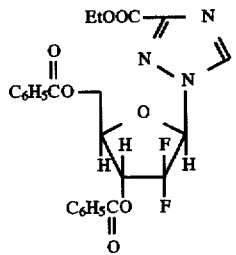

Recrystallization of "A" from ethyl acetate:isooctane provided 267 mg of the pure β-anomer in 13% yield.

B. Ethyl 1-(2'-deoxy-2',2'-difluoro-3', 5'-di-O-benzoyl-β-D-ribofuranosyl)-1,2,4-triazole-5-carboxylate (855 mg, 41.5 percent yield).

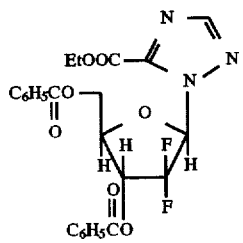

EXAMPLE 15

Preparation of alpha-anomer enriched ethyl 1-(2'-deoxy-2',2'-difluoro-3', 5'-di-O-benzoyl-D-ribofuranosyl)-1,2,4-triazole-3-carboxylate in acetonitrile Ethyl 1,2,4-triazole-3-carboxylate (0.0719 g, 0.502 mmol) was suspended in acetonitrile (1.0 ml) and treated with sodium hydride (0.024 g, 0.502 mmol) and stirred under a nitrogen atmosphere at 25° C. to form the sodium salt of the triazole.

2-deoxy-2,2-difluoro-D-ribofuranosyl-3, 5-dibenzoyl-1-β-(p-bromobenzene)sulfonate (0.200 g, 0.355 mmol), in acetonitrile (1.0 ml), was added to the above salt and the entire mixture was reacted for 40 hours at 50° C. to form a blocked nucleoside. HPLC analysis confirmed completion of the reaction and indicated an alpha to beta anomeric ratio of 7:1.

EXAMPLE 16

Preparation of beta-anomer enriched 2-deoxy-2, 2-difluoro-D-ribofuranosyl-1-β-(2-amino-6-chloropurine) in dimethylacetamide To a suspension of 2-amino-6-chloropurine (82.6 mmol, 14.0 g) in dimethylacetamide (900 ml) at 0° C. under nitrogen was added powdered potassium hydroxide (99.12 mmol, 5.55 g). The mixture was stirred for 30 minutes to form a solution. 2-deoxy-2,2-difluoro-D-ribofuranosyl-3, 5-dibenzoyl-1-α-iodide (82.6 mmol, 40.31 g) in dimethylacetamide (450 ml) was added. The reaction was allowed to warm to room temperature and stirred under nitrogen overnight.

The product was extracted by adding ethyl acetate and brine. The organic layer was washed successively with 1N HCl, saturated sodium bicarbonate solution, $H_2O$, and brine. The organic layer was then dried over sodium sulfate and evaporated in vacuo.

The crude product was purified with silica gel chromatography to yield a 3:1 beta to alpha anomer ratio of 2-deoxy-2,2-difluoro-D-ribofuranosyl-3, 5-dibenzoyl-1-(2-amino-6-chloropurine) $^1$H NMR (300 MHz, $CD_3OD$), δ 4.68(m, 2H, 4'—H, 5'a—H), 4.90(m, 1H, 5'b—H), 6.02(m, 1H, 3'—H), 6.29 (m, 1H, 1'—H), 7.53(m, 6H, Bz), 7.92(s, 1H, 8'—H), 8.05(m, 4H, Bz).

The dibenzoyl intermediate (0.49 mmol, 260 mg) was deprotected by suspending it in methanol at 0° C. and saturating the mixture with anhydrous ammonia. The resulting solution was warmed to room temperature and stirred overnight. The solution was then purged with nitrogen and evaporated. The titled product was then purified by washing with a non-polar solvent such as methylene chloride to remove the benzoate by products. The beta anomer was separated by reversed phase HPLC.

$^1$H NMR (300MHz, $CD_3OD$), ∂3.90(m, 3H, 4'—H,5'—H), 4.58(m, 1H, 3'—H), 6.27 (dd, 1H, 1'—H), 8.31 (s, 1H, 8—H).

The present invention has been described in detail, including the preferred embodiments thereof. However, it will be appreciated that those skilled in the art, upon consideration of the present disclosure, may make modifications and/or improvements on this invention that fall within the scope and spirit of the invention as set forth in the following claims.

What is claimed is:

1. A stereoselective anion glycosylation process for preparing an alpha-anomer enriched nucleoside of the formula

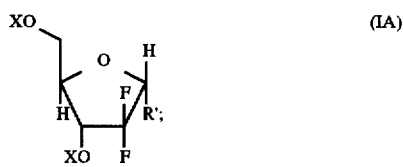
(IA)

wherein each X is independently selected from hydroxy protecting groups and R' is a nucleobase selected from the group consisting of

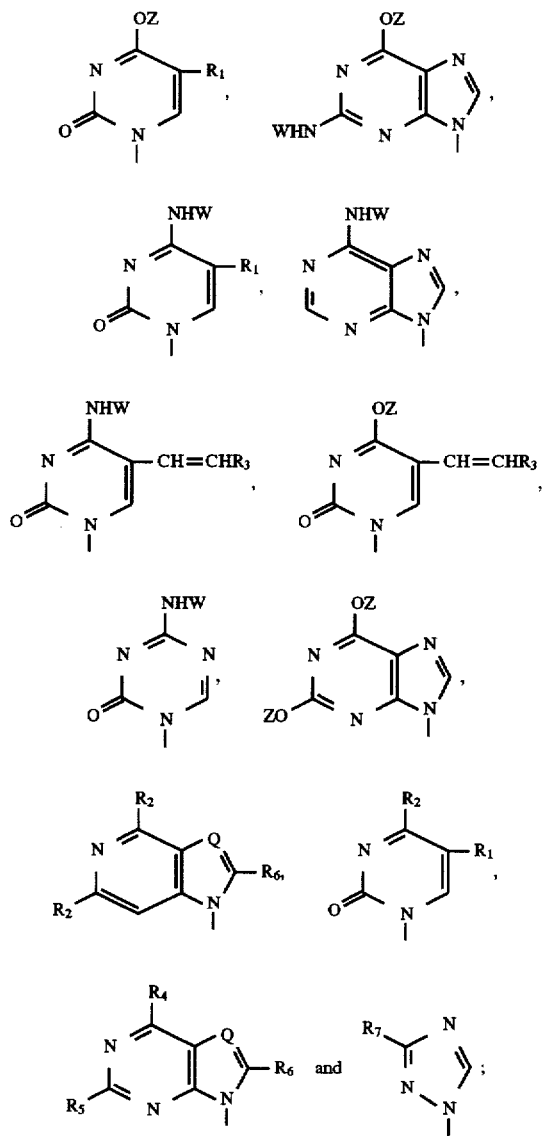

wherein $R_1$ is selected from the group consisting of hydrogen, alkyl, substituted alkyl and halo; $R_2$ is selected from the group consisting of hydroxy, halo, azido, primary amino and secondary amino; $R_3$ is selected from the group consisting of hydrogen, alkyl and halo; $R_4$, $R_5$ and $R_6$ are independently selected from the group consisting of hydrogen, —OZ, —NHW, N(alkyl)W, halo, alkoxy and thioalkyl; $R_7$ is selected from the group consisting of hydrogen, halo, cyano, alkyl, alkoxy, carboalkoxy, thioalkyl, thiocarboxamido and carboxamido; Q is selected from the group consisting of CH, $CR_8$ and N; wherein $R_8$ is selected from the group consisting of halo, carboxamido, thiocarboxamido, alkoxycarbonyl and nitrile; Z is a hydroxy protecting group and W is an amino protecting group; comprising reacting a beta-anomer enriched 2,2-difluorocarbohydrate of the formula

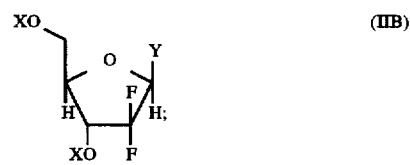
(IIB)

wherein Y is selected from the group consisting of iodo, bromo, alkylsulfonyloxy, substituted alkylsulfonyloxy, arylsulfonyloxy and substituted arylsulfonyloxy and each X is as defined above; with at least a molar equivalent of a salt of a nucleobase derivative (R") selected from the group consisting of

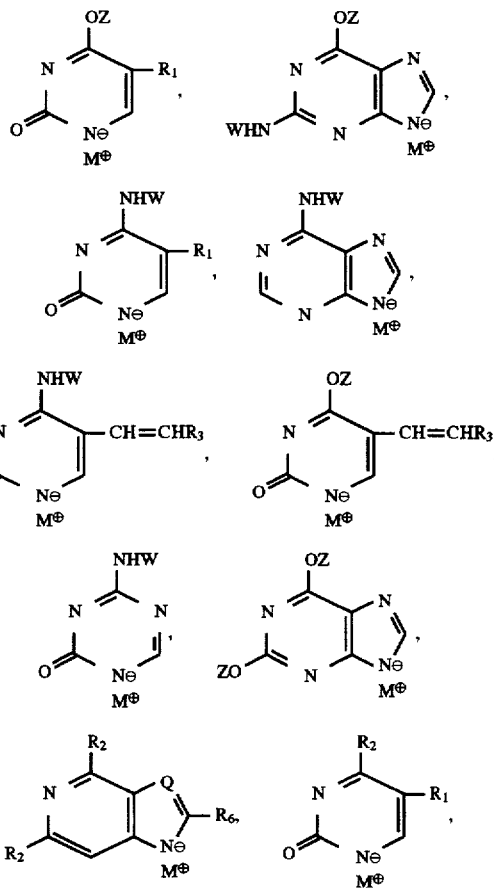

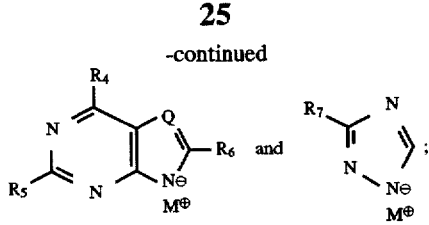 and 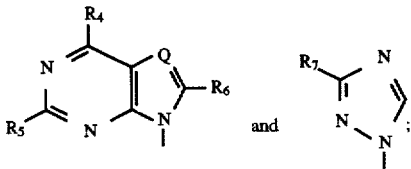

wherein R₁ through R₇, Q, Z and W are as defined above and M⁺ is a cation; in an inert solvent.

2. The process of claim 1 wherein the nucleoside is (9) regioisomer-α-anomer enriched 1-(2'-deoxy-2', 2'-difluoro-3',5'-di-O-benzoyl-D-ribofuranosyl-2, 6-dipivalamidopurine.

3. The process of claim 1 further comprising deblocking to form an alpha-anomer enriched nucleoside of the formula

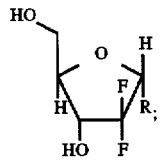 (VIA)

wherein R is a deblocked nuclebase selected from the group consisting of

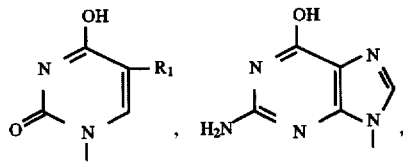

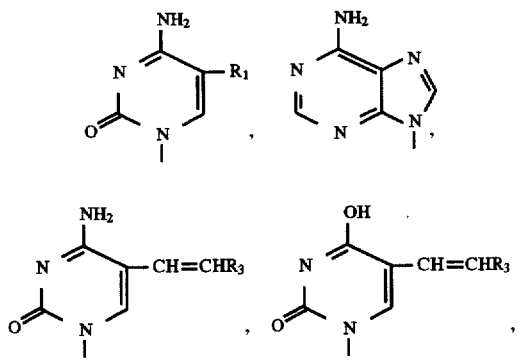

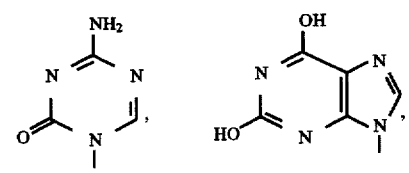

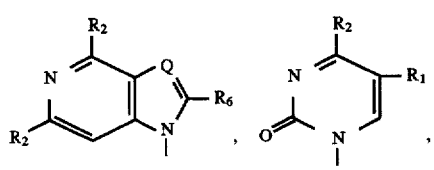

wherein R₁ is selected from the group consisting of hydrogen, alkyl, substituted alkyl and halo; R₂ is selected from the group consisting of hydroxy, halo, azido, primary amino and secondar amino; R₃ is selected from the group consisting of hydrogen, alkyl and halo; R₄, R₅ and R₆ are independently selected from the group consisting of hydrogen, —OH, —NH₂, N(alkyl), halo, alkoxy and thioalkyl; R₇ is selected from the group consisting of hydrogen, halo, cyano, alkyl, alkoxy, carboalkoxy, thioalkyl, thiocarboxamide and carboxamide; Q is selected from the group consisting of CH, CR₈ and N; and wherein R₈ is selected from the group consisting of halo, carboxamide, thiocarboxanide, alkoxycarbonyl and nitrile.

4. A stereoselective anion glycosylation process for preparing an alpha-anomer enriched nucleoside of the formula

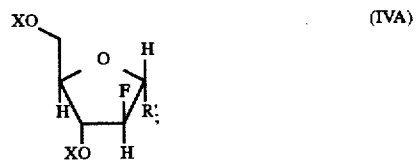 (IVA)

wherein each X is independently selected from hydroxy protecting groups and R' is a nucleobase selected from the group consisting of

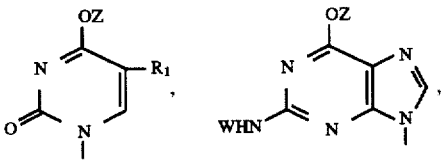

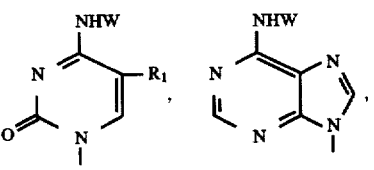

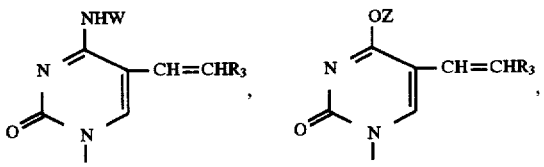

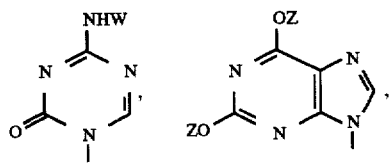

-continued

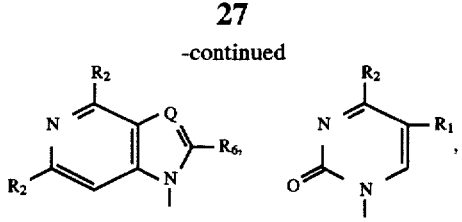

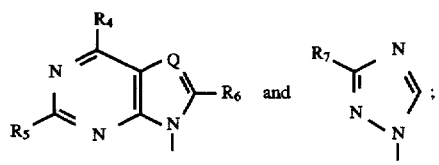

wherein $R_1$ is selected from the group consisting of hydrogen, alkyl, substituted alkyl and halo; $R_2$ is selected from the group consisting of hydroxy, halo, azido, primary amino and secondary amino; $R_3$ is selected from the group consisting of hydrogen, alkyl and halo; $R_4$, $R_5$ and $R_6$ are independently selected from the group consisting of hydrogen, —OZ, —NHW, N(alkyl)W, halo, alkoxy and thioalkyl; $R_7$ is selected from the group consisting of hydrogen, halo, cyano, alkyl, alkoxy, alkoxycarbonyl, thioalkyl, thiocarboxamido and carboxamido; Q is selected from the group consisting of CH, $CR_8$ and N; wherein $R_8$ is selected from the group consisting of halo, carboxamido, thiocarboxamido, alkoxycarbonyl and nitrile; Z is a hydroxy protecting group and W is an amino protecting group; comprising reacting a beta-anomer enriched 2-fluorocarbohydrate of the formula

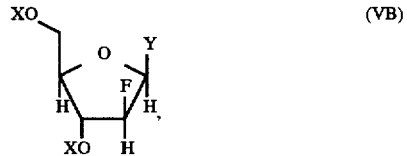 (VB)

wherein Y is selected from the group consisting of iodo, bromo, alkylsulfonyloxy, substituted alkylsulfonyloxy, aryl-sulfonyloxy and substituted arylsulfonyloxy and X is as defined above; with at least a molar equivalent of a salt of a nucleobase derivative (R") selected from the group consisting of

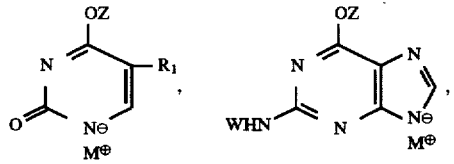

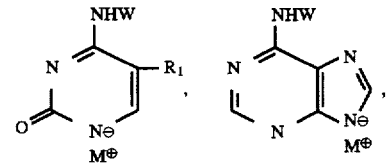

-continued

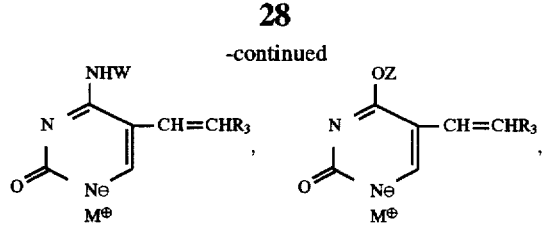

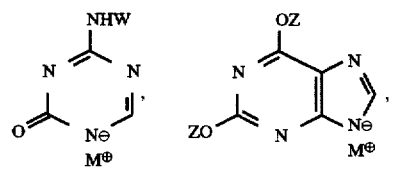

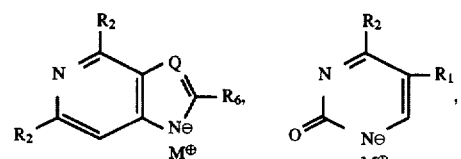

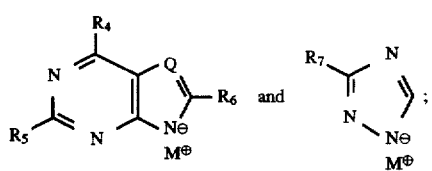

wherein $R_1$ through $R_7$, Q, Z and W are as defined above and $M^+$ is a cation; in an inert solvent.

5. The process of claim 4 further comprising deblocking to form an alpha-anomer enriched nucleoside of the formula

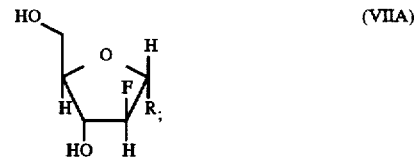 (VIIA)

wherein R is a deblocked nuclebase selected from the group consisting of

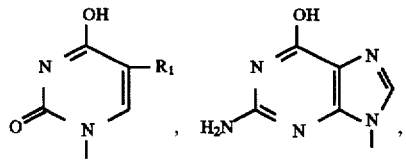

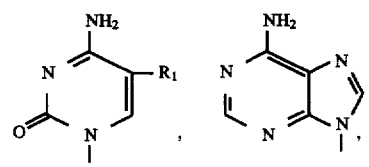

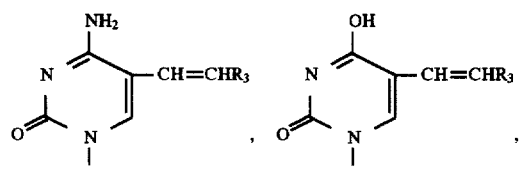

-continued

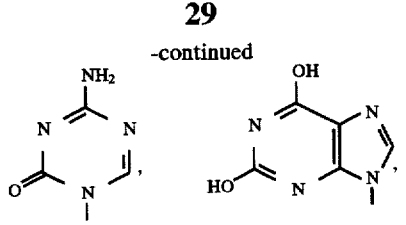

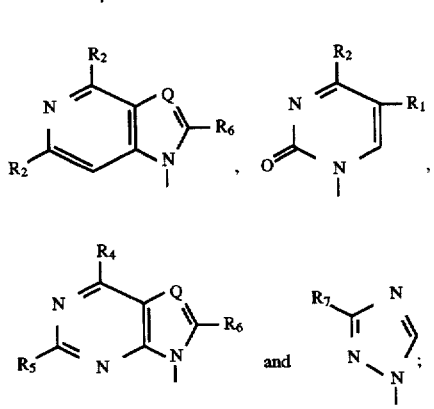

wherein $R_1$ is selected from the group consisting of hydrogen, alkyl, substituted alkyl and halo; $R_2$ is selected from the group consisting of hydroxy, halo, azido, primary amino and secondar amino; $R_3$ is selected from the group consisting of hydrogen, alkyl and halo; $R_4$, $R_5$ and $R_6$ are independently selected from the group consisting of hydrogen, —OH, —NH$_2$, N(alkyl), halo, alkoxy and thioalkyl; $R_7$ is selected from the group consisting of hydrogen, halo, cyano, alkyl, alkoxy, carboalkoxy, thioalkyl, thiocarboxamido and carboxamido; Q is selected from the group consisting of CH, CR$_8$ and N; and wherein $R_8$ is selected from the group consisting of halo, carboxamido, thiocarboxamido, alkoxycarbonyl and nitrile.

6. A stereoselective anion glycosylation process for preparing a beta-anomer enriched nucleoside of the formula

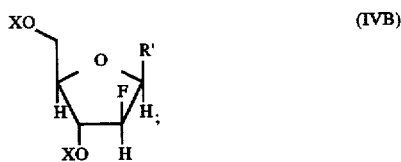

(IVB)

wherein each X is independently selected from hydroxy protecting groups and R' is a nucleobase selected from the group consisting of

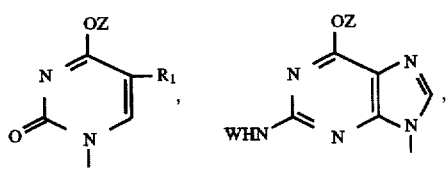

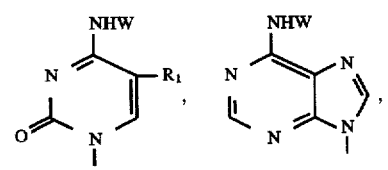

-continued

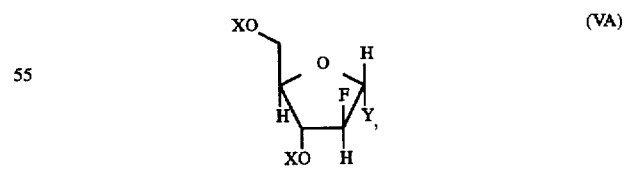

wherein $R_1$ is selected from the group consisting of hydrogen, alkyl, substituted alkyl and halo; $R_2$ is selected from the group consisting of hydroxy, halo, azido, primary amino and secondary amino; $R_3$ is selected from the group consisting of hydrogen, alkyl and halo; $R_4$, $R_5$ and $R_6$ are independently selected from the group consisting of hydrogen, —OZ, —NHW, N(alkyl)W, halo, alkoxy and thioalkyl; $R_7$ is selected from the group consisting of hydrogen, halo, cyano, alkyl, alkoxy, alkoxycarbonyl, thioalkyl, thiocarboxamido and carboxamido; Q is selected from the group consisting of CH, CR$_8$ and N; wherein $R_8$ is selected from the group consisting of halo, carboxamido, thiocarboxamido, alkoxycarbonyl and nitrile; Z is a hydroxy protecting group and W is an amino protecting group; comprising reacting an alpha-anomer enriched 2-fluoro carbohydrate of the formula (VA)

wherein Y is selected from the group consisting of iodo, alkylsulfonyloxy, substituted alkylsulfonyloxy, arylsulfonyloxy and substituted arylsulfonyloxy and each X is as defined above; with at least a molar equivalent of a salt of a nucleobase derivative (R") selected from the group consisting of

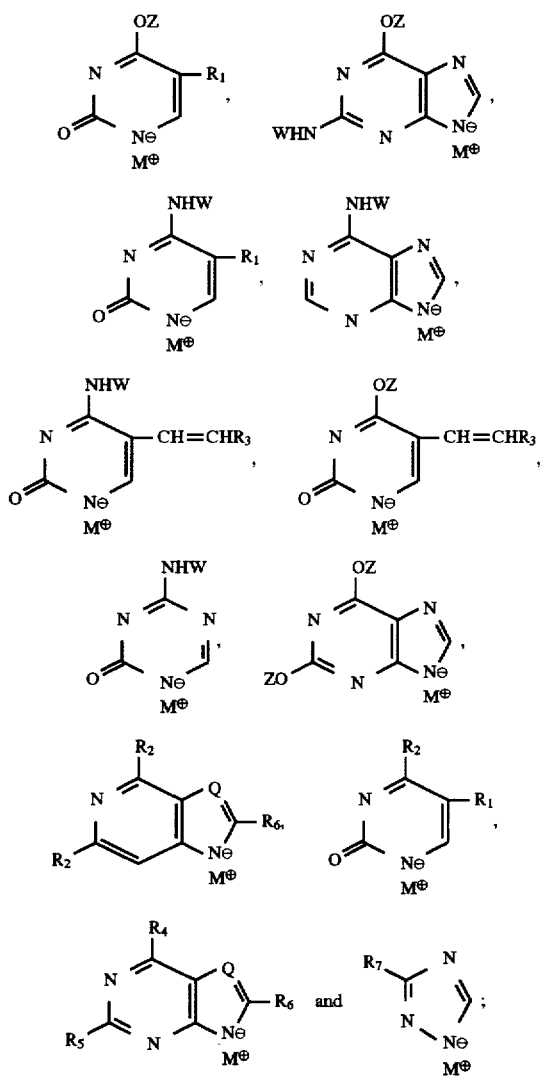

wherein $R_1$ through $R_7$, Q, Z and W are as defined above and $M^+$ is a cation; in an inert solvent.

7. The process of claim 6 wherein the amount of R" is from about 1 molar equivalent to about 10 molar equivalents.

8. The process of claim 6 wherein Z and W are pivalamido.

9. The process of claim 6 wherein X is selected from the group consisting of benzoyl, mono-substituted benzoyl, di-substituted benzoyl, acetyl, pivaloyl and t-butyldimethylsilyl.

10. The process of claim 6 wherein $M^+$ is sodium or potassium metal cation.

11. The process of claim 6 wherein Y is selected from the group consisting of iodo, p-bromobenzenesulfonyloxy and p-nitrobenzenesulfonyloxy.

12. The process of claim 6 wherein the solvent is selected from the group consisting of dichloromethane, 1,2-dichloroethane, dichlorofluoromethane, acetone, toluene, anisole, chlorobenzene, dimethylformamide, acetonitrile, N,N-dimethylacetamide, methanol, tetrahydrofuran, ethyl acetate, dimethylsulfoxide and mixtures thereof.

13. The process of claim 6 wherein the reaction temperature is from about 23° C. to about 130° C.

14. The process of claim 6 further comprising deblocking to form a beta-anomer enriched nucleoside of the formula

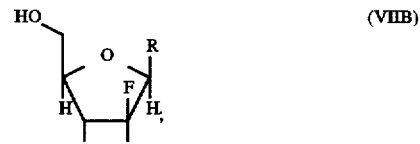

(VIIIB)

wherein R is a deblocked nuclebase selected from the group consisting of

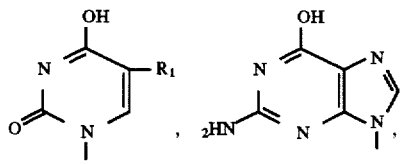

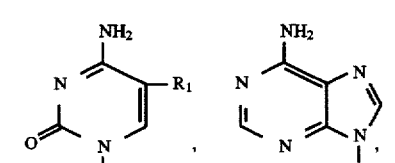

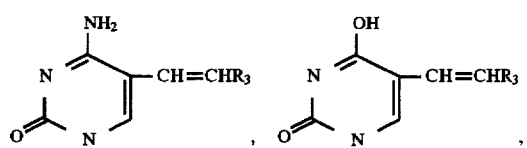

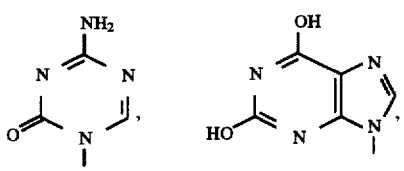

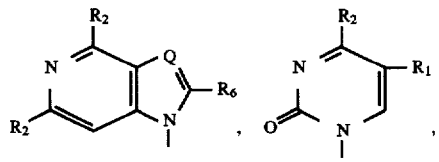

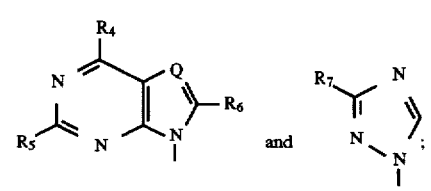

wherein $R_1$ is selected from the group consisting of hydrogen, alkyl, substituted alkyl and halo; $R_2$ is selected from the group consisting of hydroxy, halo, azido, primary amino and secondar amino; $R_3$ is selected from the group consisting of hydrogen, alkyl and halo; $R_4$, $R_5$ and $R_6$ are independently selected from the group consisting of hydrogen, —OH, —NH$_2$, N(alkyl), halo, alkoxy and thioalkyl; $R_7$ is selected from the group consisting of hydrogen, halo, cyano, alkyl, alkoxy, carboalkoxy, thioalkyl, thiocarboxamido and carboxamido; Q is selected from the group consisting of CH, CR$_8$ and N; and wherein R$_8$ is selected from the group consisting of halo, carboxamido, thiocarboxamido, alkoxycarbonyl and nitrile.

* * * * *